US009497609B2

(12) United States Patent
Otto et al.

(10) Patent No.: US 9,497,609 B2
(45) Date of Patent: Nov. 15, 2016

(54) PERSONAL MONITORING SYSTEM AND METHOD

(71) Applicant: Integrity Tracking, LLC, Boca Raton, FL (US)

(72) Inventors: Chris A. Otto, Huntsville, AL (US); Chirag D. Patel, Chicago, IL (US); Corey L. Sanders, Madison, AL (US)

(73) Assignee: Integrity Tracking, LLC, Boca Raton, FL (US)

( * ) Notice: Subject to any disclaimer, the term of this patent is extended or adjusted under 35 U.S.C. 154(b) by 0 days.

(21) Appl. No.: 14/546,781

(22) Filed: Nov. 18, 2014

(65) Prior Publication Data

US 2015/0072640 A1 Mar. 12, 2015

Related U.S. Application Data

(63) Continuation of application No. 13/539,296, filed on Jun. 29, 2012, now Pat. No. 8,938,210.

(60) Provisional application No. 61/502,654, filed on Jun. 29, 2011.

(51) Int. Cl.

| | |
|---|---|
| ***H04M 11/04*** | (2006.01) |
| ***H04W 4/22*** | (2009.01) |
| ***H04W 4/02*** | (2009.01) |
| ***G06F 19/00*** | (2011.01) |
| *H04W 64/00* | (2009.01) |
| *H04B 17/00* | (2015.01) |
| *H04W 4/20* | (2009.01) |
| *H04L 29/08* | (2006.01) |
| *H04M 1/725* | (2006.01) |

(52) U.S. Cl.

CPC ............ *H04W 4/22* (2013.01); *G06F 19/3418* (2013.01); *H04W 4/02* (2013.01); *H04B 17/0085* (2013.01); *H04L 67/12* (2013.01); *H04M 1/72538* (2013.01); *H04M 2250/10* (2013.01); *H04M 2250/12* (2013.01); *H04W 4/028* (2013.01); *H04W 4/20* (2013.01); *H04W 64/00* (2013.01)

(58) Field of Classification Search

CPC ....... H04W 4/22; H04W 4/02; H04W 4/028; H04W 4/20; H04W 64/00; H04B 17/0085; G06F 19/3418; H04L 67/12; H04M 1/72538; H04M 2250/10; H04M 2250/12

USPC .......... 455/404.2, 404.1, 456.1, 456.5, 456.6

See application file for complete search history.

(56) References Cited

U.S. PATENT DOCUMENTS

2003/0171860 A1* 9/2003 Fan ........................ G01S 5/0027 701/32.3

2011/0215903 A1* 9/2011 Yang ...................... G01C 21/20 340/8.1

2015/0173037 A1* 6/2015 Pijl ....................... A61B 5/1117 455/456.1

* cited by examiner

*Primary Examiner* — Khai M Nguyen

(74) *Attorney, Agent, or Firm* — Ann I. Dennen

(57) ABSTRACT

A personal monitoring device of the present disclosure has a sensing device that detects motion of a user and a global positioning system (GPS) that executes queries to identify a current location of the user. In addition, the device has logic that stores motion data indicative of motion of the user detected by the sensing device and adjusts a rate of location queries executed by the GPS based upon the stored motion data indicative of motion.

15 Claims, 9 Drawing Sheets

800

All Events | Username (#)

| | Date/Time 801 | Type 802 | Description 803 | Heartrate 804 | Skin Temperature 805 | Body Position 806 |
|---|---|---|---|---|---|---|
| 808 | Wed Jun 15 2012 at 12:38 PM CDT | Normal | Alarm cleared for Username on Wed Jun 15 2012 at 12:38 PM CDT) | 65 | 91 | Vertical |
| 809 | Wed Jun 14 2012 at 12:39 PM CDT 807 (MAP) | Severe | Username panicked on Wed Jun 15 2012 at 12:39 PM CDT) | 100 | 89 | Horizontal |
| 810 | Wed Jun 14 2012 at 12:40 PM CDT (MAP) | Severe | Username panicked on Wed Jun 15 2012 at 12:40 PM CDT) | 100 | 89 | Horizontal |

FIG. 8

PERSONAL MONITORING SYSTEM AND METHOD

CROSS REFERENCE TO RELATED APPLICATIONS

This application is a continuation of and claims priority to U.S. patent application Ser. No. 13/539,296, entitled "Personal Monitoring System and Method" and filed on Jun. 29, 2012, and this application claims priority to U.S. Provisional Patent Application Ser. No. 61/502,654, entitled "A System Architecture for A Mobile Personal Emergency Response and Health Monitoring System" and filed on Jun. 29, 2011, both of which are fully incorporated herein by reference.

BACKGROUND

It is customary for elderly individuals that are at risk of falling, or individuals that have medical conditions that may require fast emergency response and immediate access to medical attention, to rely on and utilize personal emergency response systems (PERS) to request this assistance. Traditionally, these systems are coupled to an individual's home communications infrastructure such as the public switched telephone network (PSTN) or more recently a broadband Internet connection. One such architecture is described in U.S. patent application Ser. No. 12/686,342, entitled Human Health Monitoring Systems and Methods, which is incorporated herein in its entirety.

When an emergency happens, it is imperative that assistance gets dispatched quickly to the person regardless of the location. Current technologies available allow for assistance to be given to a person if the person is at specific location when they need the assistance or for a person to be capable of finding assistance themselves if they are away from those locations.

BRIEF DESCRIPTION OF THE DRAWINGS

The invention can be better understood with reference to the following drawings. The elements of the drawings are not necessarily to scale relative to each other, emphasis instead being placed upon clearly illustrating the principles of the invention. Furthermore, like reference numerals designate corresponding parts throughout the several views.

FIG. 8 is an exemplary graphical user interface (GUI) listing historical data displayed by the system such as is depicted in FIG. 1.

DETAILED DESCRIPTION

The present disclosure relates to a personal emergency response system that enables a user employing the system to obtain help during an emergency. The personal emergency response system comprises a monitor that is worn and/or in close proximity to the user during times when the user is at risk for needing assistance if an emergency event occurs, e.g., when the user is alone at his/her residence.

During use, the monitor senses and records user characteristic data indicative of physiological, motion, and location characteristics related to the user. The monitor transmits the user characteristic data to a computing device over a network, e.g., a cellular network, to a computing device.

The data received by the computing device is stored and is available for real-time or subsequent access. The computing device may notify a caregiver of the received characteristic data or notify the caregiver of events that occur as evidenced by the characteristic data received. Based upon the information received by the caregiver, the caregiver may contact the user. In one embodiment, the caregiver may contact via a network the monitoring device via a number specifically assigned to the monitoring device similar to a mobile phone number. In one embodiment, in response to a call, the monitor automatically creates a network connection with the caregiver and activates a speakerphone through which the caregiver can speak with the user. In addition, the caregiver can contact additional individuals designated as emergency contacts and/or request an emergency response team to the user. In one embodiment, the monitor records data of the user's location (e.g., global positioning system data) which the computing device stores and which can be used to locate the user if the user's whereabouts are unknown.

Figure 1:
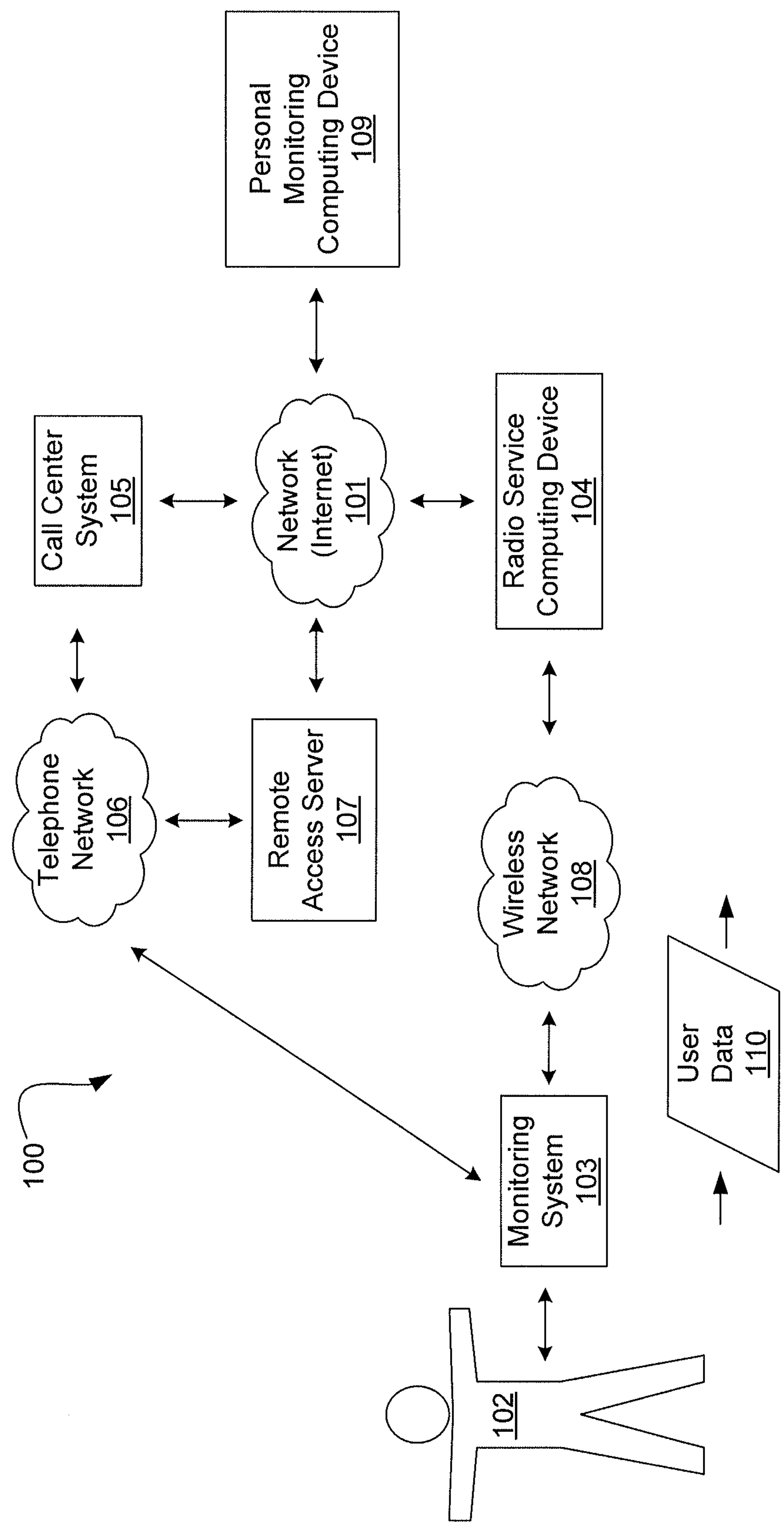
FIG. 1 is a block diagram of an exemplary personal monitoring system in accordance with an embodiment of the present disclosure.

FIG. 1 is a block diagram of an exemplary personal monitoring system 100 in accordance with an embodiment of the present disclosure. The system 100 comprises a monitoring device 103 that is worn on or kept in close proximity to a user 102. In addition, the system 100 comprises a radio service computing device 104 and a personal monitoring computing device 109 that communicate via a network 101. Further, the system 100 comprises a call center system 105 that is accessible via the internet 101 and a remote access server 107, each of which is accessible by the personal monitoring computing device 109. The call center 105 and the remote access server 107 each may communicate with the monitoring system 103 via the telephone network 106.

Figure 2:
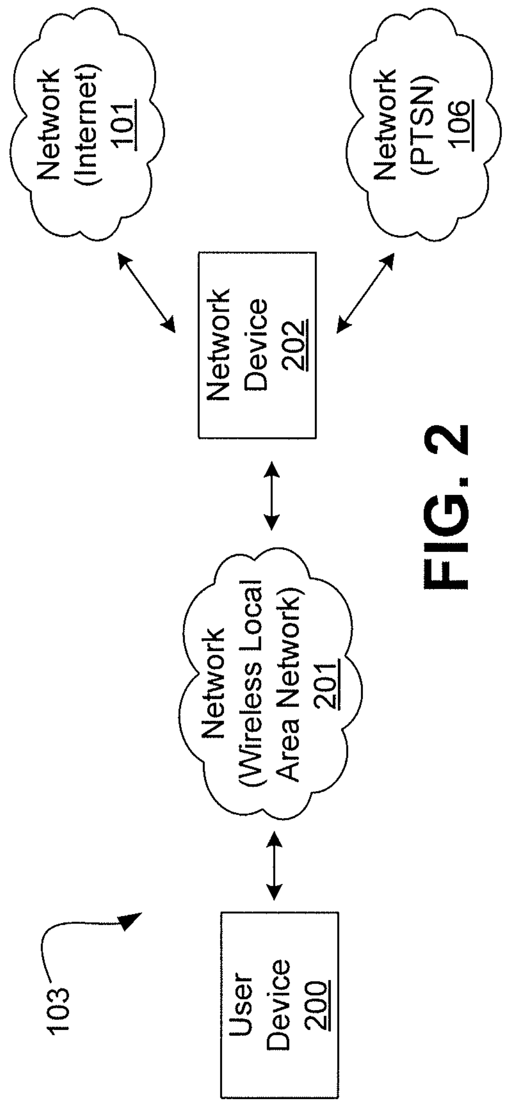
FIG. 2 is a block diagram of an exemplary monitoring system such as is depicted in FIG. 1.

The monitoring system 103, described further with reference to FIG. 2, automatically monitors the user. In this regard, the monitoring system 103 collects the characteristic data related to the user, which may include but is not limited to physiological, motion, and location data, hereinafter collectively referred to as "user data."

The monitoring system 103 transmits collected user data 110 to a radio service computing device 104 via a wireless network 108. The radio service computing device 104 transmits the user data to the personal monitoring computing device 109 via the network 101.

The personal monitoring computing device 109 stores the user data 110 received via the network 101. In addition to storing the user data 110, the personal monitoring computing device 109 may analyze the user data 110 received and determine if an event has occurred, e.g., the user 102 falls, and send a notification to the call center system 104 via the network 101. If such a notification is made, the call center system 105 may automatically create a connection, e.g., a voice connection, to the monitoring system 103 via the telephone network 106 or a caregiver may be monitoring the call center system 105 and manually place a phone call to the monitoring system 103 via the telephone network 106. In addition, the personal monitoring computing device 109 may connect to the monitoring system 103 through the remote access server 107 via the telephone network 106.

In one embodiment, the wireless network 108 is a mobile device network. The mobile device network may be, for example, a cellular network, that communicates via radio waves. In one embodiment, the user device 200 may communicate over a public switched telephone network (PSTN). In such a configuration, a user of a mobile device (not shown) may connect to any other phone (mobile or land line) in the world. Other configurations may be employed in other embodiments. For example, the monitoring system 103 may communicate with the personal monitoring computing device 109 via satellite technology.

In one embodiment, the network 101 is the Internet. However, other types of networks may be used in other embodiments to implement the system 100. In this regard, any type of packet-switched networks may be used that connect the radio service computing device 104 to the personal monitoring computing device 109.

In one embodiment, the telephone network 106 is a public switched telephone network (PSTN). The PSTN is a collection of circuit-switched telephone networks that may employ various technologies for communicating, e.g., telephone lines, fiber optic lines, microwave, cellular towers, and/or satellites. Note that in one embodiment the wireless network 108 may be a part of the telephone network 106. However, for illustration of the system 100 of the present disclosure, no such linkage or inclusion is shown in FIG. 1.

FIG. 2 is a block diagram illustrating an exemplary monitoring system 103. The monitoring system 103 comprises a user device 200 and a networking device 202 that communicate via a network 201, e.g., a wireless local area network (LAN). The network device 202 may be configured to connect to the telephone network 106 (e.g., PSTN) and/or the network 101 (e.g., Internet). The network device 202 is described further with reference to FIG. 4.

The user device 200 may be any type of device that is worn by the user 102 (FIG. 1). The user device 200 may be any type of device that senses, stores, and transmits user data 110 and enables the user 102 to be contacted (or to contact) a caregiver for assistance. An exemplary user device may include, but is not limited to a mobile phone (including a smart phone), belt clip, chest strap, pendant, watch, and/or arm band, for example.

In one embodiment, the user device 200 comprises a mechanism (not shown) that enables the user 102 to quickly and easily request help. Such a mechanism may include, but is not limited to a manual push button that when selected automatically dials a caregiver (or someone who can contact the caregiver for the user 102).

In one embodiment, the user device 200 comprises a battery to provide power for the device. In one embodiment, the user device 200 comprises a global positioning system (GPS) for obtaining location data (not shown) describing the precise location of the user 102. In one embodiment, the user device 200 comprises mobile network interface equipment (such as a global system for mobile communication (GSM) or code division multiple access (CDMA) radio) that enables the user device 200 to transmit user data 110 (including location information, such as latitude and longitude data) via the wireless network 108 and provide 2-way communication between the user 102 and the call center system 105 (FIG. 1) via the network 106. In one embodiment, the device 200 further comprises a sensor (e.g., an accelerometer or barometric pressure sensor) that performs motion analysis and fall detection so that the user data 110 may contain data indicative of motion data related to the user. Such a device/system is described in U.S. patent application Ser. No. 12/192,855 entitled Wearable Health Monitoring Device and Methods for Fall Detection, U.S. patent application Ser. No. 12/192,830 entitled Wearable Health Monitoring Device and Methods for Step Detection (the '830 application) and U.S. patent application Ser. No. 12/192,855 entitled Wearable Health Monitoring Device and Methods for Fall Detection (the '855 application), which are incorporated herein by reference in their entirety.

Additionally, the user device 200 may be configured to detect whether the user 102 has fallen. If a fall occurs, the user device 200 may establish a telephone connection via the network 106 with the call center computing device 105. The device may also utilize an accelerometer to provide activity measurement and steps as described in the '830 application; an ECG circuit to monitor heart rate; a thermometer to read temperature; and a barometric pressure sensor for measuring elevation. Such a user device 200 is described in the '830 application, the '855 application, and U.S. patent application Ser. No. 12/972,039 entitled Wireless Sensor Network System and Method (the '039 application), which are incorporated herein by reference in their entirety.

In one embodiment, the network 201 is a wireless local area network (WLAN). In such an embodiment, the network 201 links the user device 200 with the networking device 202 via a wireless communication method, such as, for example Bluetooth or Zigbee®.

Figure 4:
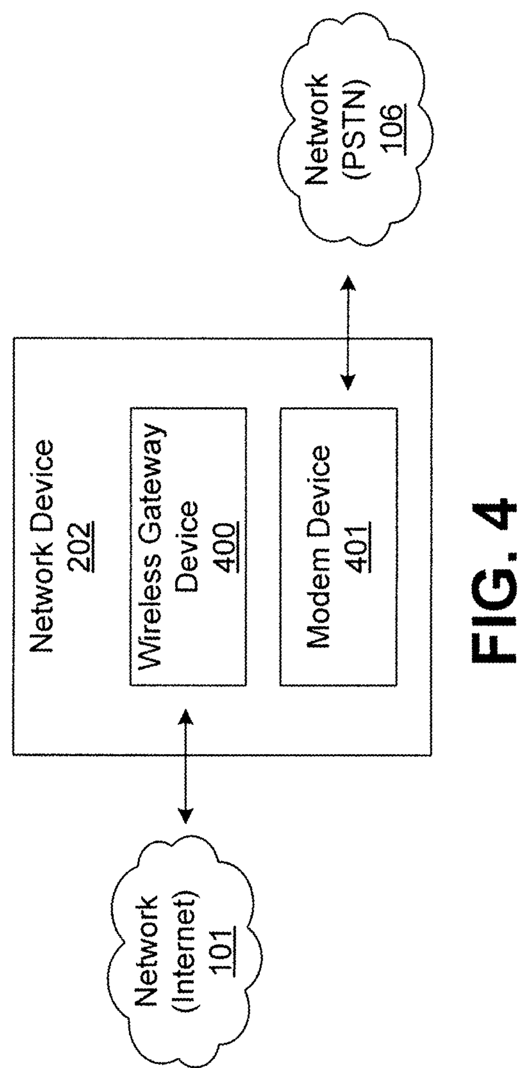
FIG. 4 is a block diagram of a network device such as is depicted in FIG. 2.

With reference to FIG. 4, in one embodiment, the networking device 202 comprises a wireless gateway device 400 and a modem 401. The wireless gateway device 400 is a computing device that routes packets from the network 201 to the network 101 (e.g., the Internet). The wireless gateway device 400 may serve as a wireless access point to the network 101, a router, and/or a firewall. The modem 401 may be any type of digital subscriber line (DSL) modem or cable modem that connects the WLAN 201 to the network 101.

Thus, with reference to FIG. 1, the user device 200 may connect to and communicate with the personal monitoring computing device 109 through the wireless network 108 and the network 101 using radio communication methods and the radio service computing device 104. In addition, the user device 200 may communicate with the personal monitoring computing device 109 through the network 201 and the network 101 using radio communication methods and the network device 202. Furthermore, the user device 200 may contact or be contacted by the call center computing device 105. Such contact may be established, for example, when the call center computing device 105 establishes a connection with a telephone number assigned to the user device 200 (e.g., a cell phone or mobile number).

Figure 3:
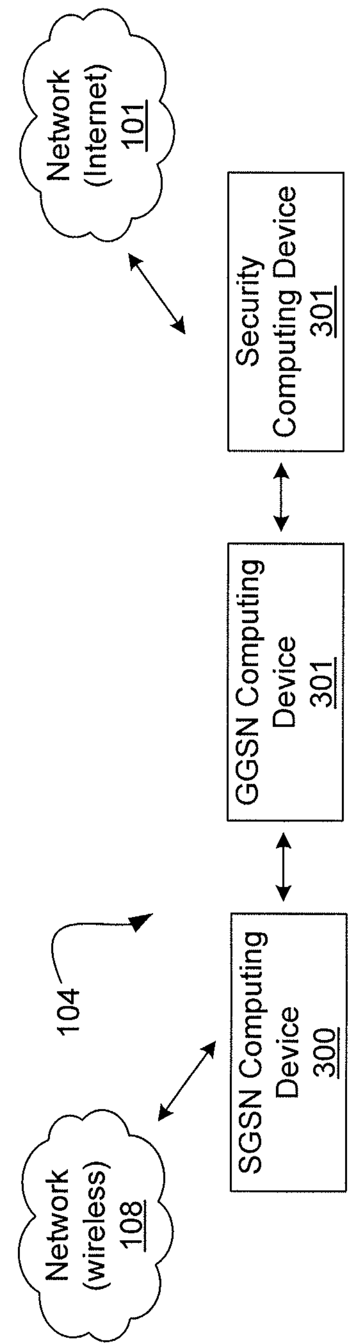
FIG. 3 is a block diagram of an exemplary radio service computing device such as is depicted in FIG. 1.

FIG. 3 depicts an exemplary embodiment of a radio service computing device 104. The exemplary radio service computing device 104 is a general packet radio service (GPRS) radio service computing device 104 that comprises a serving GPRS support node (SGSN) computing device 300, a gateway GPRS service node (GGSN) computing device 301, and a security computing device 301, e.g., a firewall. Note that in such an embodiment, the GPRS is a packet mobile data service that enables communication on the global system for mobile communications (GSM). In this regard, the GPRS computing device 104 allows mobile networks, e.g., 2G, 3G, 4G, WCDMA, etc., to transmit internet protocol (IP) packets to the network 101 (FIG. 1).

During operation, the SGSN computing device 300 receives data user data 110 (e.g., in the form of packets) from the user device 200 via the network 108, translates the user data 110 received, and performs authentication of the user 102. The GGSN computing device 301 converts the user data 110 into the appropriate packet data protocol (PDP) format (e.g., IP or X.25) and sends them out on the corresponding network 101. Further, data may be sent to the user device 200 (FIG. 2) via the network 108. In this regard, data packets (not shown) received from the network 101 addressed to the user device 200 are translated to GSM standard data packets.

Note that the radio service computing device 104 is depicted and described as an exemplary embodiment. Other technologies, protocols, and/or types of systems may be used to connect the user device 200 employing mobile communication methods to the network 101, e.g., the Internet.

Figure 5:
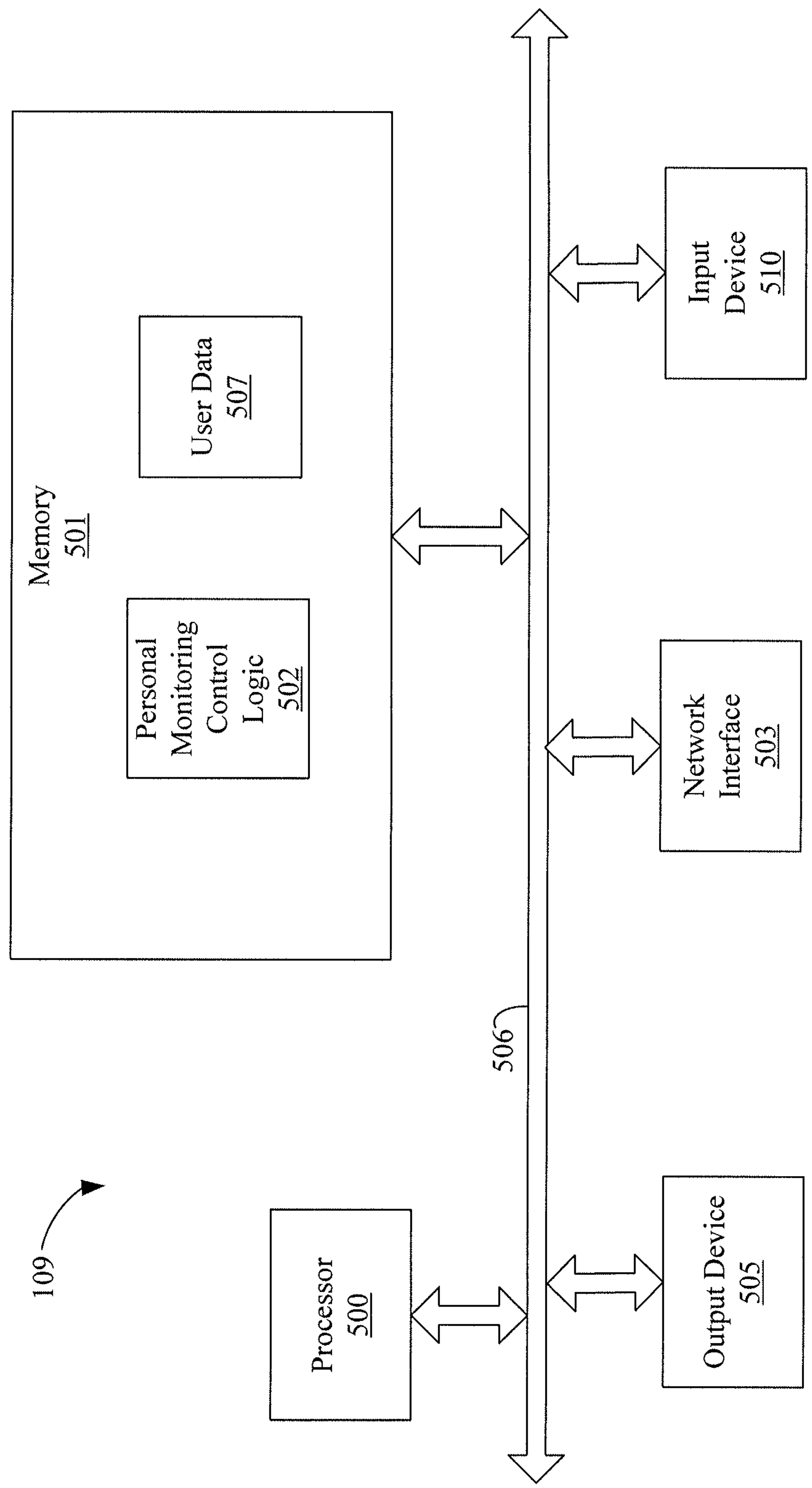
FIG. 5 is a block diagram of an exemplary personal monitoring computing device such as is depicted in FIG. 1.

FIG. 5 depicts an exemplary embodiment of the personal monitoring computing device 109. The personal monitoring computing device 109 comprises personal monitoring control logic 502 for generally controlling the operation and functionality of the personal monitoring computing device 109. In the exemplary embodiment shown by FIG. 5, control logic 502 is implemented in software and stored in memory 501. In other embodiments, the control logic 502 may be implemented in firmware, hardware, or any combination of software, firmware, and/or hardware.

The personal monitoring computing device 109 further comprises user data 507 stored in memory 501. The user data 507 stores user data 110 and other data related to the user 102, including any data determined based upon the user data 110 received from the user device 200.

The exemplary embodiment of the personal monitoring computing device 109 depicted by FIG. 5 includes a processor 500, which comprises processing hardware for executing instructions stored in memory 501. The processor 500 communicates to and drives the other elements within the personal monitoring computing device 109 via a local interface 506, which can include at least one bus.

Furthermore, the personal monitoring computing device 109 comprises a network interface 503. The network interface 503 may be any type of communication device that communicatively couples the personal monitoring computing device 109 with the network 101 (FIG. 1) and the call center computing device 105 and the remote access a server 107.

In addition, the personal monitoring computing device 109 comprises an output device 505. The output device 505 may be any type of device known in the art or future-developed that provides data to a user (or caregiver) using the personal monitoring computing device 109. As a mere example, the display device 305 may be a liquid crystal display (LCD).

Furthermore, the personal monitoring computing device 109 comprises an input device 510. The input device 510 may be, for example, a keyboard.

The personal monitoring control logic 502 receives user data 110, which includes data indicative of physiological data 611 (FIG. 6), motion data 614 (FIG. 6), and location data 623 (FIG. 6), and stores the user data 110 as user data 507. An exemplary personal monitoring computing device 109 is described in U.S. patent application Ser. No. 12/686,352, entitled Wireless Sensor Network System and Method for Using Same (the '352 application), and U.S. patent application Ser. No. 12/686,296, entitled Human Health Monitoring Graphical User Interface Systems and Methods (the '296 application), each of which is incorporated herein by reference in its entirety.

During operation, the personal monitoring control logic 502 analyzes the user data 507. In this regard, the personal monitoring control logic 502 may take action if the data 507 indicates the necessity. As an example, the personal monitoring control logic 502 may notify the call center system 105 via the network 101 that an event (e.g., a fall) has occurred that needs immediate attention, based upon the user data 507.

In one embodiment, the personal monitoring control logic 502 displays to the output device 605 a graphical user interface (GUI) (not shown) that enables a user of the personal monitoring computing device 109 to view user data 507 and/or take action based upon the viewed user data 507. One such GUI is described in the '296 application. In one embodiment, the personal monitoring control logic 502 displays a dashboard (not shown) where a user can view user data 507 indicative of past or present information about the user 102. Such a display may be in the form of a chronological list (not shown), which is a timeline of events for which user data 507 has been received and/or generated.

The GUI may further display location information contained in the user data 507 to the user of the personal monitoring computing device 109. In this regard, the personal monitoring control logic 502 may calculate a person's location, described further herein, based upon user data 507 indicative of latitude and longitude information. In particular, the user data 506 is periodically updated and/or modified with additional information available provided by the user device 200.

An exemplary display of such information is shown with reference to FIG. 8. FIG. 8 depicts a GUI 800 in the form of a table comprising headers "Date/Time" header 801, "Type" header 602, "Description" header 603, "Heart rate" header 604, "Skin Temperature" header 605, and "Body Position" header 606. In the exemplary GUI 800, the user data 507 is displayed in chronological order with a first row 808 being the most recent post and a third row 810 being the oldest post.

Each of the entries 808-810 comprises a subset of the user data 507 indicative of present and historical information. Further, one or more of the entries 808-810 may comprise location information obtained from the user data 507. In one embodiment, a hyperlink 807 is included in the entry 809. When selected, the personal monitoring control logic 502 displays a map, e.g., a Google map. Thus, the personal monitoring control logic 502 may use the user data 507 to dynamically render a graphical map with the user's current location at the time of the occurrence described in the entry 808-810.

Figure 9:
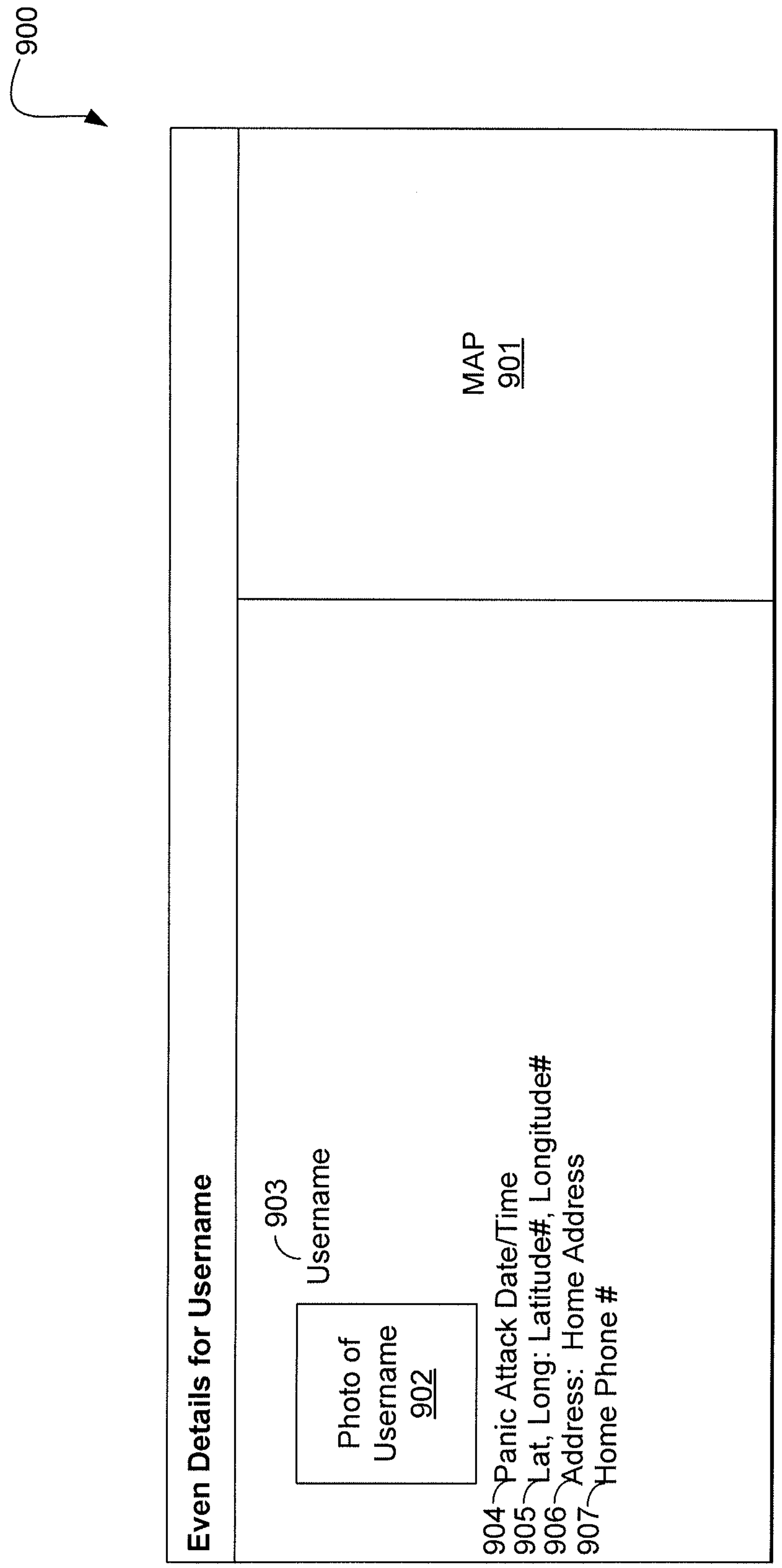
FIG. 9 is an exemplary graphical user interface (GUI) listing event details displayed by the system such as is depicted in FIG. 1.

FIG. 9 depicts a GUI 900 that may be displayed by the personal monitoring control logic 502 when the user of the personal monitoring computing device 109 selects the hyperlink 807. In the embodiment depicted in FIG. 9, the GUI 900 comprises a photograph of the user 102 (FIG. 1). In addition, the GUI 900 comprises a graphical representation of a map 901. Other information may also be displayed, for example, the personal monitoring control logic 502 may display a description of the event 904, latitude and longitude values 905, home address of the user 906, and home address phone number 907, which may be a land line or a mobile number.

Figure 6:
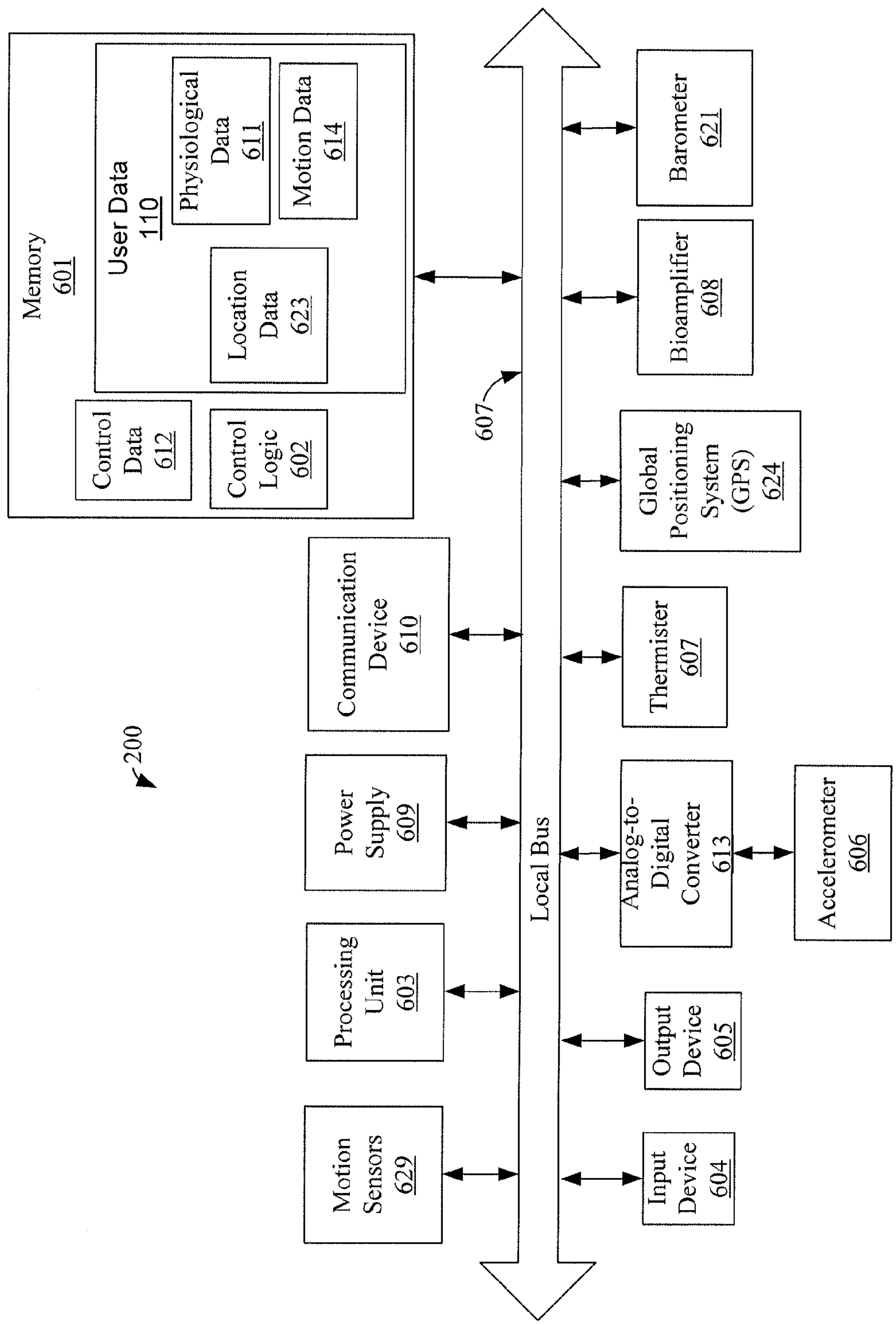
FIG. 6 is a block diagram of an exemplary user device such as is depicted in FIG. 2.

FIG. 6 is a block diagram depicting an exemplary user device 200 of the present disclosure. The exemplary user device 200 comprises a processor 603, an output device 605, an input device 604, a communication device 610, and a power supply 609. In addition, the exemplary user device 200 comprises a thermistor 607, one or more bioamplifiers 608, barometer 612, and other motion sensors 629. Each of these components communicates over local interface 607, which can include one or more buses. Furthermore, the user device 200 comprises an accelerometer 606 and an analog-to-digital converter (ADC) 613. Further, the user device 200 comprises a global positioning system (GPS) 624.

The other motion sensors 629 may include additional accelerometers or inertia sensors, for example. Any type of motion sensor known in the art or future-developed may be used to detect motion of the user 102 (FIG. 1).

User device 200 further comprises control logic 602, user data 110, and control data 612. The user data 110 may include physiological data 611, motion data 614, and location data 623. Control logic 602 can be software, hardware, or a combination thereof. In the exemplary user device 200 shown in FIG. 6, control logic 602, is shown as software stored in memory 601. Memory 601 may be of any type of memory known in the art, including, but not limited to random access memory (RAM), read-only memory (ROM), flash memory, and the like.

As noted hereinabove, control logic 602, physiological data 611, motion data 614, and control data 612 are shown in FIG. 6 as software stored in memory 601. When stored in memory 601, control logic 602, physiological data 611, motion data 614, and control data 612 can be stored and transported on any computer-readable medium for use by or in connection with an instruction execution system, apparatus, or device, such as a computer-based system, processor-containing system, or other system that can fetch the instructions from the instruction execution system, apparatus, or device and execute the instructions.

In the context of the present disclosure, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium Processor 603 may be a digital signal processor (DSP) or other type of circuitry configured to run the control logic 602 by processing and executing the instructions of the control logic 602.

The communication device 610 may be, for example, a low-powered radio device, e.g., a radio semiconductor, radio frequency antenna (RF antenna); a wired communication device such a RS232, USB, or Ethernet; or other wireless communication device, such as a magnetic communications scheme or infrared scheme; or any type of communication device, which communicatively couples the user device 200 personal monitoring computing device 109.

In an embodiment having a data-receiving unit 302, physiological data 611 and motion data 614 can be relayed in a real-time manner, a periodic manner, an "as they occur" fashion, or some combination of the three. For example, a serious condition such as an individual falling could be relayed to the central monitoring device 305 (FIG. 3).

In one embodiment, the bioamplifier 608 is a device that interfaces with the electrodes 200. Thus, the bioamplifier 608 gathers, amplifies, filters and conditions the signal integrity of human physiological activity for use by the control logic 602. The signals (not shown) collected by the bioamplifier 608 from the electrodes 200 relate to the nervous system of the user 301 (FIG. 3). In one embodiment, the signals collected are stored as the physiological data 611, and are used by the control logic 602.

The output device 605 is a device for communicating information to the user 102 (FIG. 1). The output device 605 may be, for example, an LED that indicates that power is on. In addition, the output device 605 may be a speaker that emits a sound upon the occurrence of a particular event, e.g., when the battery needs to be charged or upon activation.

Physiological data 611 includes data obtained from the one or more sensors, e.g., the thermistor 607 or the bioamplifier 608. Hence, the physiological data 611 comprises data indicative of physiological aspects of the user 301 (FIG. 3). Examples of physiological data 611 include data indicative of ECG readings, heartbeat readings, temperature readings, or the like.

Motion data 614 includes data obtained from the accelerometer 606. Hence, the motion data 614 comprises data indicative of movement of the user. In the 3-axis accelerometer embodiment, the motion data 614 includes data indicative of the user 301 in an X-direction, Y-direction, and the Z-direction.

The input device 604 enables the user 102 to enter data into the user device 200. In the exemplary user device 200, the input device 604 may be a push button. When the push button is selected, the user device 200 generates a message which is sent over the networks 108 and 101 to the personal monitoring computing device 109 as an emergency event. Other input devices may be used in other embodiments. For example, the input device 604 may be a keyboard or a touch screen for performing particular operations on the user device 200.

In one embodiment, the input device 604 is a microphone (not shown), and an exemplary output device 605 is a speaker (not shown), as described hereinabove. In such an embodiment, the speaker and the microphone enable the user 102 to be in communication with the call center system 105 or the caregiver (not shown). In such an example, the user device 200 detects an event, such as, for example, a fall or a negative change in the user's physiological condition based upon physiological data 611. The personal monitoring computing device 109 receives user data 110 that includes the physiological data 611 and transmits an alert to the call center system 105 or the caregiver. The call center system 105 or caregiver may then contact the user 102 over the network 106 via the microphone/speaker input/output arrangement.

The thermistor 607 is conductively coupled to a metal contact (not shown). The thermistor 607 is a device that measures a skin temperature of the user 102 where the thermistor 607 is in contact with the metal contact, which is in contact with the skin of the user 102. In one embodiment, the thermistor 607 is a thermocouple (not shown).

In one embodiment, the accelerometer 606 is a 3-axis accelerometer for monitoring motion. The accelerometer 606 may be a direct current ("DC") response or a non-DC response accelerometer. In one embodiment, the accelerometer 606 is a microelectromechanical ("MEMS") piezoresistive technology sensor (not shown), however other types of accelerometers known in the art or future-developed may be used in other embodiments of the user device 200.

In one embodiment, the accelerometer 606 measures acceleration due to gravity and physical movement and transmits the raw analog signals to the ADC 613. The ADC 613 translates the received analog into digital data indicative of the received analog signals (not shown). The ADC 613 provides the digital data indicative of the analog signals to the control logic 602, which can store the digital data as motion data 614. The control logic 602 then calculates and stores additional motion data 614 including activity-induced energy expenditure (AEE) and/or orientation, based upon the motion data 614. In addition, the control logic 602 can use the motion data 614 to detect a fall, detect steps made by the user 301, and categorize activity performed by the user 301. The accelerometer 606 may be a single (or dual) axis accelerometer arranged to create a three-axis orthogonal coordinate system, as depicted in FIG. 3 as X, Y, and Z axes.

During extraction of the physiological data 611 and motion data 614, the control logic 602 reacts quickly to changes in real-time and also reduces the data stream, thereby maximizing the storage capabilities of memory 601. Reducing the data stream may refer to techniques for averaging the data, or inspecting the real-time stream for certain feature extraction. One such technique is described in U.S. patent application Ser. No. 11/972,335 entitled Wireless Sensor Network Context Data Delivery System and Method.

The barometer 621 is any device that is capable of determining barometric pressure. Thus, the barometer 621 obtains a barometric pressure measurement, e.g., air pressure measurement, and the control logic 602 can calculate the user's location in reference to the user's height above sea level. Such calculated height may be stored in the user data The GPS 624 is any system that communicates with a satellite (not shown), for example, to obtain location data 623 related to where the user 102 is located. In this regard, the GPS 624 may obtain longitude and latitude data that identifies the user's location.

In one embodiment of the system 100 (FIG. 1), the user device 200 may tend to use a considerable amount of power from the power supply 609 (FIG. 6), e.g., a battery. One method of efficiently utilizing power resources is described in the '335 application.

In one embodiment of the system 100, the control logic 602 throttles GPS location queries performed by the GPS 624 (FIG. 6) based upon a first order approximation of positional change derived from a motion sensor, e.g., the accelerometer 606. In such embodiment, throttling the GPS and using data obtained from a lower power-consuming motion sensor reduces power consumption of the system 100.

In such embodiment, the control logic 602 performs a first order approximation on the motion data 614 to determine if the motion data indicates a change in the user's location. In the process, the system control logic 602 stores data indicative of the last known location obtained from GPS 624 as location data 623. In determining if a positional change has occurred, the control logic 602 samples another motion-based sensor, e.g., the accelerometer 606 (FIG. 6), which is a lower power-consuming sensor than the GPS. In one embodiment, the control logic 602 uses detected steps over a given time frame to determine if a positional change has occurred. If the number of detected steps exceeds a threshold, then the control logic 602 may query the GPS. Otherwise, the control logic 602 does not query the GPS to save power. For example, a threshold may be determined such that if the user has taken less than 100 steps in the previous hour then use the last known location. Using the last known location obtained by the GPS as opposed to the GPS querying the current location avoids using the power intensive GPS receiver to obtain a precise location when it is estimated that the user's location has not changed appreciably based upon the measured steps.

In another embodiment, the control logic 602 may look instead at the amount of expended energy over a period of time. If the user has not expended enough energy to change their location appreciably, then the control logic 602 uses the last known location of the GPS 624 instead of getting an exact current location by querying the GPS, which would expend unnecessary battery power.

Thus, in both embodiments described, the GPS 624 remains inactive or idle unless it is determined that a threshold number of steps has been taken or an appreciable amount of energy has been expended indicating that the user has moved to a location that is so different from the known location previously obtained from the GPS to justify expending energy getting a current location from the GPS. The '830 application described a method for determining the number of steps a user has taken during a given period of time.

In another embodiment, the user device 200 may not send location data 623 to the personal monitoring computing device 109 until the user device control logic 602 determines that the user's location has changed appreciably, e.g., a threshold of steps have been taken that indicates that location data 623 needs to be updated on the personal monitoring computing device 109. In such an embodiment, the control logic 602 may continue to transmit other user data 110 to the personal monitoring computing device 109 in a periodic fashion so that the personal monitoring computing device 109 may discern the scenario when the user has not changed location and the scenario when the device is not operational or out of range from a communication infrastructure.

In one embodiment, the user device 200 detects whether the user 102 has fallen or taken steps as described in the '855 application or taken steps. In such an embodiment, the control logic 602 may control periodic measurements taken from the accelerometer. In this regard, the control logic 602 may not take measurements from the accelerometer 602 until a threshold of change is determined and the acceleration ceases after a period of time.

In another embodiment, the user device 200 may extend the battery life by utilizing piezoelectric MEMS devices (not shown) that harvest kinetic energy. Such devices typically take advantage of Faraday's Law and rely on natural vibrations to move a tiny electromagnetic generator (not shown). Modern piezoelectric kinetic scavenging MEMS devices can generate several hundred microwatts of power. While perhaps not sufficient to power the user device 200 completely, the power generated may be used to augment the power subsystem and be channeled to storage in the power supply 609, e.g., the battery. Or similarly, the power generated may be used to supplement power so as to minimize draw on the power supply 609. This method would depend on the relative activity level of the user but could be used to delay charging or extend the usable life of the device between charges.

In one embodiment, the user device control logic 602 determines whether the user device 200 is being worn by the user 102 to ensure efficacy of user data 110 transmitted. In this regard, data indicating whether the user device 200 is being worn when the user data 110 is obtained may be used to aid the caregivers in helping the user 102 and provide statistics regarding problems leading to the user 102 not wearing the user device 200.

In one embodiment, the user device 200 may comprise a mechanical trigger (not shown), e.g., an actuator or switch. The mechanical trigger may be toggled when the user 102 attaches or removes the user device 200. Data indicative of such attachment and/or removal may be transmitted with the user data 110.

In another embodiment, the user device 200 may comprise a touch less proximity sensor that reacts to changes in magnetic or RF field (examples are Hall Effect sensors or an RF-capacitive human body proximity sensor which may detect a change in capacitance as a result of near proximity to a human body). In another embodiment, the user device 200 may comprise a thermal measurement instrument, e.g., thermistor 607. Since bodies naturally emit heat, detection of that heat using a thermistor, infrared receiver, or other temperature reading device can indicate that the user device 200 is being worn.

In another embodiment, the control logic 602 may record stationary movement, e.g., breathing, heart beating, scratching, muscle movement and spasms, etc. The control logic 602 may determine if the user device 200 is being worn based on such user data 110 indicative of the stationary movements In one embodiment, the control logic 200 may roam a geographical area in which the user is present to obtain data relating to available networks. In such an embodiment, the control logic 200 may select another network for use in delivering data to the personal monitoring computing device 109. When the user device 200 is not transmitting across the network 108, the user device 200 may use other networks and transmission methods to deliver user data 110 and ensure security, such as a REST POST interface as seen in the '335 application.

For example, the user device 200 may be in close proximity to a wireless network, such as an 802.11g network. The user device 200 detects the wireless network, connects to the located network automatically, and transmits data through the wireless network instead of through the network 108. Additionally, at a home or facility where there is a wireless personal area network (WPAN), such as ZigBee® or 6LoPAN, the user device 200 may transmit measurements to these WPANs and communicate with an existing emergency response system in place at other locations.

In one embodiment, the WPANs may not allow user data 110 in particular protocols generated by the user device 200. In such an embodiment, the user device 200 retains the user data 110 that the user device 200 was unable to transmit and transmits the retained user data 110 at a later time. Notably, the user device 200 may connect to multiple different WPANs at a given time. When no network is found by the control logic 602, user data 110 is stored in nonvolatile memory for later transmission. Such a system is described in the '342 application.

As described hereinabove, the control logic 602 stores location data 623 periodically that the control logic 602 sends with user data 110 to the personal monitoring computing device 109. Such location data 623 contained in the user data 110 may be used to track the location of the user 102. In this regard, a caregiver may have an itinerary of the user 102 that the user 102 is intended to follow over a period of time. Such location data 623 can be used by the caregiver to ensure that the user 102 follows the itinerary. Note that in one embodiment, the control logic 602 disables its location tracking capability so that it is unable to track the user's location.

In one embodiment, the user device 200 transmits location data 623 in the user data 110 periodically or on-demand. If the user device 200 transmits location data 623 in the user data 110 periodically (e.g., at set intervals of time), the personal monitoring control logic 502 generates user data 110 indicative of the user's location history.

If the user device 200 transmits location data 623 on demand, the personal monitoring control logic 502 transmits a notification to the user device 200, such as with short message service (SMS) or through an acknowledgement message. Upon receipt, the user device 200 queries the GPS 624 and transmits user data 110 containing the location data 623 to the personal monitoring computing device 109.

Figure 7:
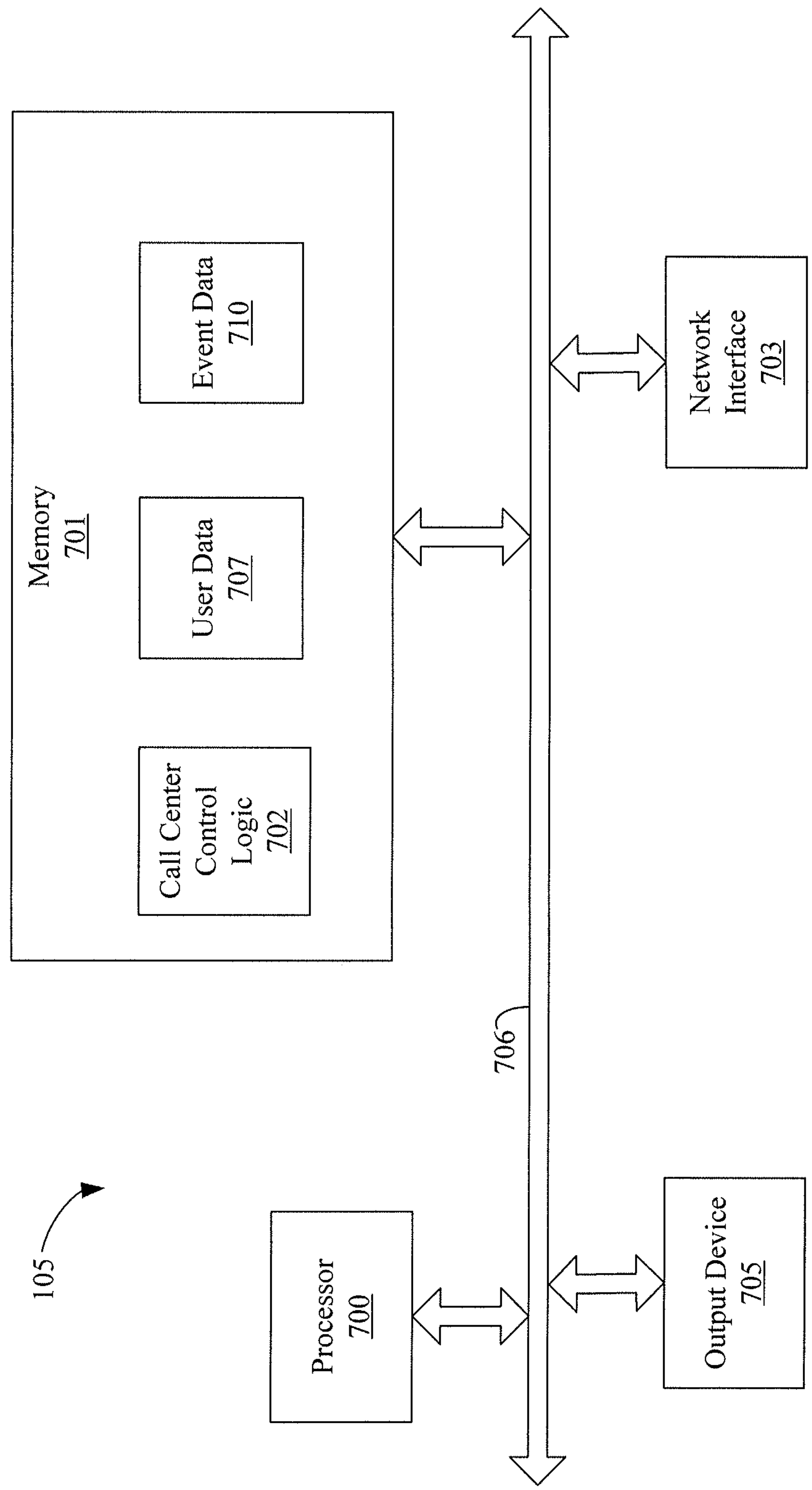
FIG. 7 is a block diagram of an exemplary call center system such as is depicted in FIG. 1.

FIG. 7 depicts an exemplary embodiment of the call center system 105. The call center system 105 comprises call center control logic 702 for generally controlling the operation and functionality of the call center system 105. In the exemplary embodiment shown by FIG. 7, call center control logic 702 is implemented in software and stored in memory 701. In other embodiments, the call center control logic 702 may be implemented in firmware, hardware, or any combination of software, firmware, and/or hardware.

The call center system 105 further comprises user data 707 stored in memory 701. The user data 707 data related to the user 102 that is received from the personal monitoring computing device 109, including any data determined by the personal monitoring computing device 109 based upon the user data 110 received from the user device 200.

The exemplary embodiment of the call center system 105 depicted by FIG. 7 includes a processor 700, which comprises processing hardware for executing instructions stored in memory 801. The processor 700 communicates to and drives the other elements within the call center system 105 via a local interface 706, which can include at least one bus.

Furthermore, the call center system 105 comprises a network interface 703. The network interface 703 may be any type of communication device that communicatively couples the call center system 105 with the network 101 (FIG. 1) and the call center system 105 and the remote access a server 107.

In addition, the call center system 105 comprises an output device 705. The output device 705 may be any type of device known in the art or future-developed that provides data to a user (or caregiver) using the call center system 105. As a mere example, the output device 705 may be a liquid crystal display (LCD).

Furthermore, the call center system 105 comprises an input device 710. The input device 710 may be, for example, a keyboard.

In one embodiment, the call center system 105 is available 24/7 to assist users in response to an event. In this regard, the call center control logic 702 receives data indicative of an event from the personal monitoring computing device 109. The call center control logic 702 stores the received event data as event data 710. The event data 710 may comprise data indicative of a type of alert, the location of the user, and/or the time the event occurred. In response, the call center control logic 702 automatically attempts to establish contact with the user 102 (FIG. 1) via the telephone network 106 directly calling the user device 200 (FIG. 2) or a user of the call center system 105 manually establishing, e.g., calling, the user device 200. If the user 102 responds to the attempted contact and requests help or the user device 200 automatically answers but no contact is made with the user 102, the user of the call center system 105 may dispatch necessary emergency responders to the user 102 based upon the location information contained in the event data 710. Notably, the control logic 602 is configured to automatically answer such a call from the call center system 105 in the event that the user 102 is unable to take action to respond to the call.

In one embodiment, the user device 200 (FIG. 2) may initiate a call to the call center system 105 once an event has occurred, for example if the user 102 is still capable of taking action or a caregiver (not shown) is with the user 102 when the event occurs. In such an embodiment, the call center control logic 702 dynamically bind, e.g., by associating data indicative of the telephone number calling obtained from a caller identification (caller ID) system with data indicative of the event that has occurred. In this regard, the event data 710 may comprise an identifier (e.g., the mobile phone number of the device 200) that the call center control logic 702 may used to associate the event data 710.

In one embodiment, the user device 200 establishes a modem call directly with the call center system 105. When the call center system 105 answers such a call, event data 710 and/or user data 707 may be transmitted after connection. When such a call is answered, the call center control logic 702 connects the call to a call center system user and switches the call to voice mode thereby establishing a voice call between the user 102 and the user and/or caregiver at the call center system 105. Such binding of the event data 710 and the incoming call from the user device 200 may further be associated with event data 710 and user data 707 obtained from the personal monitoring computing device 109.

The user device 200 may efficiently deliver the user data 110 to the personal monitoring computing device 109. In one embodiment, the user device 200 may employ a less reliable transport mechanism and a best-effort transmission policy such as provided by the User Datagram Protocol (UDP). Best-effort delivery, like that used in UDP transmissions, allows the transmissions to be connectionless. In one embodiment, data transmitted is in the form of a binary data object.

If UDP is employed, datagrams (as defined by the UDP) sent by the user device 200 may comprise a sequence number so that redundant transmissions can be identified, a timestamp to indicate when in time these measurements were taken, a type field to identify the type of measurements that are reported assuming the type reported is not always the same, and control fields to enable a simple acknowledgement system to ensure data is properly delivered. Other data that may be sent with a datagram containing the user data 110 is described with reference to the '342 application.

In one embodiment, the personal monitoring computing device 109 poles a port (not shown) on the personal monitoring computing device 109. If a datagram is received, the personal monitoring control logic 502 continues to receive and store subsequent datagrams until the last datagram (in the sequence) is received. In this regard, the personal monitoring control logic 502 will keep a running table to the last sequence number received from each user device 200 from which personal monitoring control logic 502 has received messages (with timeouts to remove an entry after a certain threshold of time has expired without activity). Thus, the personal monitoring control logic 502 can ignore duplicates receipts of user data 110. Once this has occurred, the personal monitoring control logic 502 transmits an acknowledgement to the user device 200.

In one embodiment, the personal monitoring control logic 502 may request a management operation for the user device 200 (e.g., firmware upgrade, remote provisioning, reset of device). In such an embodiment, when user data 110 is reported to the personal monitoring control logic 502, the personal monitoring control logic 502 may transmit data in the acknowledgement that indicates that a management operation is pending. For example, the personal monitoring control logic 502 may set a flag (toggle a bit) in the acknowledgement sent to the user device 200 to indicate the management operation is pending. In such an embodiment, the personal monitoring control logic 502 waits until it receives a counter acknowledgement from the user device 200 and may resend periodically if no acknowledgement is received from the user device 200. When the user device 200 receives such a flagged acknowledgement, transmits an acknowledgement to the personal monitoring control logic 502 and transmit an additional message for instruction from the personal monitoring control logic 502. Because management operations are infrequent and subsequently will not have a significant impact on overall data usage, the connection established for instruction may or may not use a different protocol, such as a REST POST interface described in the '335 application. The personal monitoring control logic 502 and the user device control logic 602 may comprise timeout logic to prevent deadlock should communications fail during transmission.

In another embodiment, the personal monitoring control logic 502 transmits an acknowledgement to the user device 200 after each user data transmission is received that contains the sequence number of the last user data 110 received. If the user device 200 does not receive the acknowledgement—in the event that the acknowledgement is either lost in transit or that the original packet never arrived at the server—it will retransmit the original user data 110 according to a particular waiting period.

In one embodiment, a Virtual Private Network (VPN) can be erected between the network 108 and the personal monitoring computing device 109 in order to protect user data 110 traveling through network 101. In one embodiment, IPSec or another protocol may be may be used to establish the VPN and encrypt the data. With this method, data is still securely transmitted end-to-end, but the additional overhead of this VPN tunnel is not borne by the expensive wireless segment of the system 100 and the user data 110 is still protected.

In one embodiment of the system 100, the personal monitoring computing device 109 uses the location data (e.g., GPS coordinates) contained in the user data 507 to identify a proper Public Service Access Point (PSAP) for the user 102 who is in need of emergency help. The PSAP is a 10-digit equivalent of 9-1-1 access and can be assigned statically into the user device 200. In addition, the personal monitoring computer device 109 may search a list of identifiers and associated PSAP numbers based upon the location of the user 102 as identified in the user data 110 received by the personal monitoring computing device 109. In one embodiment, the personal monitoring control logic 502 may determine a street address near the user 102 and perform an indexed lookup for emergency service based on street information.

In another embodiment of the system 100, the personal monitoring computing device 109 transmits location data and/or nearby street information from call center system 105. The call center system 105 may automatically determine an appropriate PSAP or a caregiver may manually find an appropriate PSAP.

In another embodiment, the user device 200 establishes not only 2-way communication, but 3-way communication as well with the call center system 105. The call center system 105 contacts the user device 200 to determine if assistance is needed. If help is desired, the Call Center establishes a 3-way call such that the user device 200 calls emergency services using e911. By utilizing the e911 system (not shown), the personal monitoring computing device 109 and the call center system 105 would never need to resolve PSAP.

In another embodiment, the system 100 provides information that a caregiver can use to locate a user 102 other than the GPS coordinates as provided by the user device 200. For example, the call center control logic 702 can display a map centered directly on the last known location (provided by GPS if outdoors or cellular triangulation to assist the GPS if indoors where GPS alone may not function) of the user 102. On such a map, the control logic 702 may highlight a nearby street or intersection or apply a circle around the location of the user 102. In one embodiment, the displayed map can overlay GPS coordinates of the user 102 with street level pictures showing what the area near the user 102 looks like and marking nearby buildings.

In one embodiment, the user data 110 received from the user device 200 may be used to calculate an elevation location of the user 102, e.g., what floor a user may be located on in a building. In this regard, the barometer 621 obtains and stores data indicative of the pressure that the control logic 602 or the personal monitoring control logic 502 may use to determine elevation location. The elevation location information, stored as location data 623, is transmitted to the personal monitoring computing device 109.

The elevation location information contained in the user data 110 may be used to determine the user's elevation above sea level. The personal monitoring control logic 502 can use the elevation information, i.e., the barometric pressure at the time the user data 110 was obtained, and translate the user data 110 containing the barometric pressure into feet to determine where (i.e., what floor) a user is located on in a building.

In addition, the personal monitoring control logic 502 may use the longitude and latitude measurements to access a service of a global elevation database. The personal monitoring control logic 502 may use the elevation data retrieved to calculate a difference between the measured elevation and the retrieved elevation to obtain the user's height above the "street level," i.e., the height above sea level for the location represented by the latitude and longitude data identifying the user's location. The difference between the height above sea level at the particular location and the user's height above sea level is transmitted to emergency personnel, either through voice or electronically, so the emergency personnel can locate the user 102. For example, the user may be 80 feet above street level, which may indicate that the user is on the $8^{th}$ floor of a building or in a treetop.

Because this information is provided verbally to emergency service responders, it will be up to the responders to interpret the details and use judgment on which floor the user may actually be located. But providing this information can save precious minutes by narrowing the search to a starting floor. In very large structures, this may mean the difference between life and death if responders cannot locate the user's floor in the structure.

Barometers are subject to a number of variations, such as temperature. In order to calculate the absolute height above sea level, the present disclosure does not necessarily require problematic, error-prone, and expensive factory calibration techniques and devices. The user device 200 circumvents using such techniques and devices by determining a baseline elevation, referred to as a "street level" elevation, and measuring the changes in elevation (i.e., height of user 102) in relation to the "street level" elevation. Thus, a caregiver can provide more definitive information to a responder about a user's location without reference to a global elevation database. In such an embodiment, the user device control logic 602 may query the accelerometer and use the result to calibrate street level as a point of reference. In this embodiment, the user device control logic 602 compares readings from the accelerometer 606 and the barometer 621 and compares those readings to threshold values, i.e., values that have been determined to indicate motion of the user, in order to determine when the user is in motion. If the user's location is changing, the user device control logic 602 samples the barometer to obtain a set of "street level" data. The user device control logic 602 may average accelerometer and the barometer data over a time interval. Thresholds for "in transit" are set so that they will not pick up movement in typical structures. For example walking around a parking garage is not sufficient movement to trigger "in transit." As an example, "in transit" could mean travelling more than a half mile in one hour. In addition, "in transit" would be set so that it is unlikely or impossible to be "in transit" while ascending or descending stairs or an elevator. In this fashion, the user device control logic 602 allows the pressure recorded at an actual event time to be compared to the pressure at last known street level calibration. The difference represents an elevation change representative of the user's approximate height above street level and can be conveyed to responders as described above. In such an embodiment, the barometer 621 need not be very accurate because we have no interest in absolute elevation above sea level. Instead, the control logic 602 determines changes in elevation (and not absolute accuracy).

In one embodiment, the control logic 602 may use a transportation map and/or database to further refine the "street level" approximation. For example, when the user device 200 determines that the user 102 is "in transit" and is at "street level," the control logic 602 may use his/her location and path of movement to determine if the user 102 is on a public transportation system such as an underground train or subway. In such a case, the user's calibrated street level is augmented with this data to determine actual street level by knowing the user was 40 feet underground during the last calibration. This adjustment could happen in real-time by communicating with the personal monitoring control logic 502 or the user device control logic 602 may adjust resolution time by delivering (either with the event or periodically) so that the personal monitoring control logic 502 can determine if the last calibrated location was in effect "street level" or if additional adjustment is required.

Figure 10:
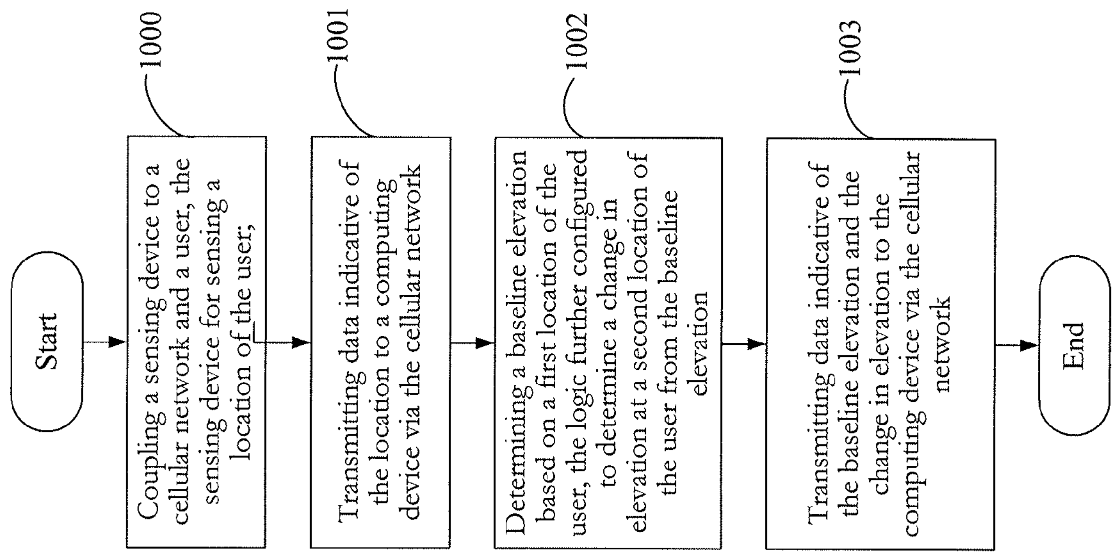
FIG. 10 is a flowchart of exemplary architecture and functionality of the system such as is depicted in FIG. 1.

FIG. 10 is a flowchart depicting exemplary architecture and functionality of the system 100.

In step 1000, a sensing device, i.e., user device 200 (FIG. 2), is coupled to a cellular network 108 (FIG. 1) and the sensing device senses a location of the user 102 (FIG. 1). In step 1001, the sensing device transmits user data 110 (FIG. 1) indicative of the location to a computing device 109 (FIG. 1) via the cellular network 108.

In step 1002, the personal monitoring control logic 602 (FIG. 6) determines a baseline elevation based on a first location of the user 102 and a change in the user's elevation based on a second location. Further, with reference to step 1002, the user device 200 transmits data indicative of the baseline elevation and the change to the personal monitoring computing device 109 via the cellular network 108 in step 1003.

What is claimed is:

1. A personal monitoring device for a user configured for avoiding using a power intensive resource when it is estimated that the user's location has not changed appreciably, comprising:

a first sensing device configured for continuously measuring movement of the user;

a global positioning system (GPS) configured for periodically executing queries to identify a current location of the user;

a processor electrically coupled to the first sensing device and to the GPS and configured for storing motion data indicative of motion of the user detected by the first sensing device in memory, wherein the memory is electrically coupled to the processor, the processor further configured for disallowing the GPS from periodically executing queries and for estimating the current location of the user based upon the stored data indicative of motion, wherein when the estimating indicates that the user has moved a certain distance from a previous location, the processor is further configured to allow the GPS to execute queries, wherein the processor is further configured for storing location data indicative of the last known location of the user as obtained by the GPS.

2. The personal monitoring device of claim 1 further comprising a housing wherein the first sensing device and the GPS are contained within the housing.

3. The personal monitoring device of claim 1, wherein the processor is further configured for estimating a positional change of the user based upon the motion data.

4. The personal monitoring device of claim 3, wherein the processor is further configured for estimating the positional change using first order approximation.

5. The personal monitoring device of claim 1, further comprising a second sensing device, the second sensing device having lower energy consumption than the first sensing device, wherein the processor is further configured for estimating steps based on data from the second sensing device.

6. The personal monitoring device of claim 1, further comprising a second sensing device, the second sensing device having lower energy consumption than the first sensing device, wherein the processor is further configured for estimating expended energy based on data from the second sensing device.

7. The personal monitoring device of claim 1, further comprising a second sensing device, the second sensing device having lower energy consumption than the first sensing device, wherein the processor is further configured for calculating an estimate of the user's activity over a time period.

8. The personal monitoring device of claim 7, wherein the processor is further configured for comparing the estimate of the user's activity over the time period to a threshold and transmitting data indicative of an estimated location of the user when the comparison exceeds the threshold.

9. A personal monitoring method for a user configured for avoiding using a power intensive resource when it is estimated that the user's location has not changed appreciably, comprising:

continuously detecting motion of a user by a first sensing device;

storing in memory data indicative of the motion detected by the first sensing device;

disallowing, by a processor electrically coupled to the first sensing device, a global positioning system (GPS) electrically coupled to the processor from executing queries for identifying a current location of the user; and estimating the current location of the user based upon the stored data indicative of motion, when the estimating indicates that the user has moved a certain distance from a previous location, allow, by the processor, the GPS to execute queries, storing, by the processor, location data indicative of the last known location of the user as obtained by the GPS.

10. The personal monitoring method of claim 9, further comprising estimating, by the processor, a positional change of the user based upon the data indicative of motion.

11. The personal monitoring method of claim 10, wherein the estimating further comprises estimating, by the processor, the positional change using first order approximation.

12. The personal monitoring method of claim 9, further comprising estimating, by the processor, steps based on data from a second sensing device, wherein the second sensing device has lower energy consumption than the first sensing device.

13. The personal monitoring method of claim 9, further comprising estimating, by the processor, expended energy based on data from a second sensing device, wherein the second sensing device has lower energy consumption than the first sensing device.

14. The personal monitoring method of claim 9, further comprising calculating, by the processor, an estimate of the user's activity over a time period based on data from a second sensing device, wherein the second sensing device has lower energy consumption than the first sensing device.

15. The personal monitoring method of claim 14, further comprising:

comparing, by the processor, the estimate of the user's activity over the time period to a threshold; and transmitting, by the processor, data indicative of an estimated location of the user when the comparison exceeds the threshold.

* * * * *